United States Patent [19]
Okuda

[11] Patent Number: 5,615,014
[45] Date of Patent: Mar. 25, 1997

[54] YARN MEASURING DEVICE

[75] Inventor: Kazuhiko Okuda, Kobe, Japan

[73] Assignee: Keisokki Kogyo Co., Ltd., Japan

[21] Appl. No.: 531,614

[22] Filed: Sep. 21, 1995

[30] Foreign Application Priority Data

Jul. 20, 1995 [JP] Japan .................................. 7-207605

[51] Int. Cl.$^6$ .................................................. G01B 11/10
[52] U.S. Cl. ......................... 356/429; 356/384; 356/238
[58] Field of Search ...................................... 356/238, 429,
356/384, 385, 355; 250/559.24

[56] References Cited

U.S. PATENT DOCUMENTS

| 3,709,610 | 1/1973 | Kruegle ................................. 356/384 |
| 4,948,260 | 8/1990 | Felix et al. ............................ 356/429 |

FOREIGN PATENT DOCUMENTS

| 117825 | 4/1994 | Japan ................................... 356/384 |

OTHER PUBLICATIONS

Nichols, R.H. "Dynamic Wire Measurements by new inspection Techniques", Technical Notes and Research Briefs, The Journal of the Acoustical Society of America, vol. 46, No. 2(Part 1) 1969 (no month) pp. 314–315.

*Primary Examiner*—Richard A. Rosenberger
*Attorney, Agent, or Firm*—Sixbey, Friedman, Leedom & Ferguson, P.C.; David S. Safran

[57] ABSTRACT

A device is provided whereby, when measuring yarn which has hairs, it is possible to detect data for the hairy part and data for the core part individually. The yarn measuring device is provided with a means which forms a Fourier transformation pattern, including a yarn core part pattern and a surface projection pattern, on a spectrum plane, by performing a Fourier transformation on diffracted laser light which has intersected and passed through traveling yarn; a first light detecting means which receives only one of the core part pattern and the surface projection pattern; and a second light detecting means which receives only the other pattern.

7 Claims, 4 Drawing Sheets

YARN MEASURING DEVICE

FIELD OF THE INVENTION

The present invention relates to a yarn measuring device employing laser light and in particular relates to a device for measuring the core part and the hairy part of traveling yarn.

BACKGROUND OF THE INVENTION

Conventionally, in spinning processes, yarn which is fed from a spinning machine and is being wound onto a winder, for example, or traveling yarn in other spinning and weaving processes or in the laboratory are measured, and defects relating to evenness or uniformity of the yarn, for example thick irregularities or thin irregularities, are detected, and furthermore periodic irregularities and the amount of hairiness are detected.

For example, there is known a device for detecting the thickness of yarn by passing traveling yarn between a pair of electrodes which are arranged facing each other, and by measuring the electrical capacitance detected by the electrodes (referred to as an electrical capacitance measuring device hereinbelow). On the other hand, as shown in U.S. Pat. No. 3264922, there is known a device for measuring the thickness of yarn by passing traveling yarn between a light source comprising a lamp and a light receiving means comprising a photocell, which are arranged facing each other, and by measuring the amount of light detected by the light receiving means (referred to as an optoelectric measuring device hereinbelow).

However, such conventional electrical capacitance measuring devices and optoelectric measuring devices only measure the overall yarn, including the core part of the yarn (main part of the yarn), and the thin hairs which project from the surface of said core part, and they are therefore unsuitable for measuring yarn which has a large degree of hairiness.

As is well known, spinning yarn has hairs at the surface of the yarn, and the aim of measuring thick irregularities and/or thin irregularities of the yarn is to investigate evenness or uniformity of the cross sectional area of the core part. If such irregularities exceed the permitted range then this will adversely affect the appearance of the cloth, and furthermore skin touch will be impaired and coloring irregularities may also result. Furthermore, if the yarn has significant thin irregularities then the tensile strength of the yarn will be reduced, and this will lead to yarn breakage during weaving. In this regard, since conventional electrical capacitance measuring devices and optoelectric measuring devices measure the whole of the yarn including the hairs, it is not possible to measure accurately thick irregularities and/or thin irregularities of the core part excluding the hairs.

On the other hand, defects in spinning yarn are not restricted to the abovementioned thick irregularities and/or thin irregularities, but also involve the state of hairs projecting from the surface of the yarn. Accordingly, if the hairs are unnecessarily plentiful or long then the warp and weft yarns will become entangled during weaving, reducing the ability to weave cloths. Further, the appearance of the woven cloth will not be good. In this regard, conventional electrical capacitance measuring devices and optoelectric measuring devices cannot detect such hair defects in independently.

On the contrary, bulky spun yarn which is soft to the touch must have sufficient hairs, and if there are too short or few hairs then this is a defect. However, with conventional electrical capacitance measuring devices and optoelectric measuring devices it is not possible to measure the state of the hairs independetly.

A device in which the optoelectrical measuring device has been improved is proposed in British Patent Application No. GB2064106A. According to this, a light source which emits scattered light onto the yarn, and a light receiving device which takes in the state of the exposure resulting from the yarn are provided, the construction is such that local lightness conditions are analyzed by means of a plurality of photosensors which are provided finely in the light receiving device, and it is explained that it is therefore possible to measure not only the core part of the yarn but also the hairy part.

However, according to the device of this British Patent Application it is necessary, in order to increase the measuring accuracy, to arrange a correspondingly large number of photosensors in matrix form, and therefore the cost is extremely high. Furthermore, since it detects the state of exposure of the yarn, stray light which is dispersed and reflected by the surface of the yarn is liable to have an effect, and there is therefore the problem that it is not possible to measure the state of the hairs accurately.

SUMMARY OF THE INVENTION

An object of the present invention is to provide a yarn measuring device with which it is possible to measure the state of the core part of the yarn and the state of the hairy part of the yarn accurately and independently by employing laser light.

According to a first teaching of the present invention, there is provided a yarn measuring device comprising: a laser light output means which emits laser light in such a manner that it intersects traveling yarn; a Fourier transformation convex lens which forms a Fourier transformation pattern, including a core part pattern and a surface projection pattern of the yarn, on a spectrum plane by performing a Fourier transformation of diffracted light which has passed through the yarn; a removal means which is located on said spectrum plane and removes one of the core part pattern and the surface projection pattern in the Fourier transformation pattern; a first light detecting means which receives the other pattern which has passed through the spectrum plane and has not been removed by said removal means; a guide means which leads the pattern which has been removed by said removal means in a direction which is refracted from the spectrum plane; and a second light detecting means which receives the pattern which has been led by said guide means.

According to a mode of embodiment of the present invention it is possible to provide a correction means which, based on the pattern data detected by the first light detecting means and the pattern data detected by the second light detecting means, corrects one set of data by means of the other set of data.

According to another mode of embodiment of the present invention the construction can be such that there is provided a reverse Fourier transformation convex lens which performs a reverse Fourier transformation on the other pattern which has passed through the spectrum plane and has not been removed by said removal means, and such that a partial image of the yarn, formed by means of said reverse transformation, is detected by the first light detecting means.

According to yet another mode of embodiment of the present invention the construction can be such that there is provided a reverse Fourier transformation convex lens which performs a reverse Fourier transformation on the pattern which has been led by said guide means, and such that a partial image of the yarn, formed by means of said reverse transformation, is detected by means of the second light detecting means.

Further, according to a second teaching of the present invention, there is provided a yarn measuring device comprising: a yarn surface state measuring device having a first laser output means which emits laser light in such a manner that it intersects traveling yarn; a first Fourier transformation convex lens which forms a first Fourier transformation pattern, including a core part pattern and a surface projection pattern of the yarn, on a first spectrum plane by performing a Fourier transformation on diffracted light which has passed through the yarn; a first removal means which is located on said first spectrum plane and removes the core part pattern from the Fourier transformation pattern; and a first light detecting means which receives the surface projection pattern which has passed through said first removal means: and a core state measuring device having a second laser output means which emits laser light in such a manner that it intersects said yarn from an angle which is different from that of said first laser output means; a second Fourier transformation convex lens which forms a second Fourier transformation pattern, including a core part pattern and a surface projection pattern of the yarn, on a second spectrum plane by performing a Fourier transformation of diffracted light which has passed through the yarn; a second removal means which is located on said second spectrum plane and removes the surface projection pattern from the Fourier transformation pattern; and a second light detecting means which receives the core part pattern which has passed through said second removal means.

According to a mode of embodiment of the present invention, it is possible to provide a correcting means which, based on surface projection pattern data detected by the first light detecting means and core part pattern data detected by the second light detecting means, corrects one set of data by means of the other set of data.

According to another mode of embodiment of the present invention, the construction can be such that there is provided a first reverse Fourier transformation convex lens which performs a reverse Fourier transformation on the surface projection pattern which has passed through the first removal means, and such that a yarn surface projection image, formed by means of said reverse transformation, is detected by the first light detecting means.

According to yet another mode of embodiment of the present invention, the construction can be such that there is provided a second reverse Fourier transformation lens which performs a reverse Fourier transformation on the core part pattern which has passed through the second removal means, and in that a yarn core part image, formed by means of said reverse transformation, is detected by means of the second light detecting means.

BRIEF DESCRIPTION OF THE DRAWINGS

FIGS. 1a, 1b and 1c illustrate the optical principle applicable to the present invention.

DETAILED DESCRIPTION OF THE PREFERRED EMBODIMENTS

Figure 1A:
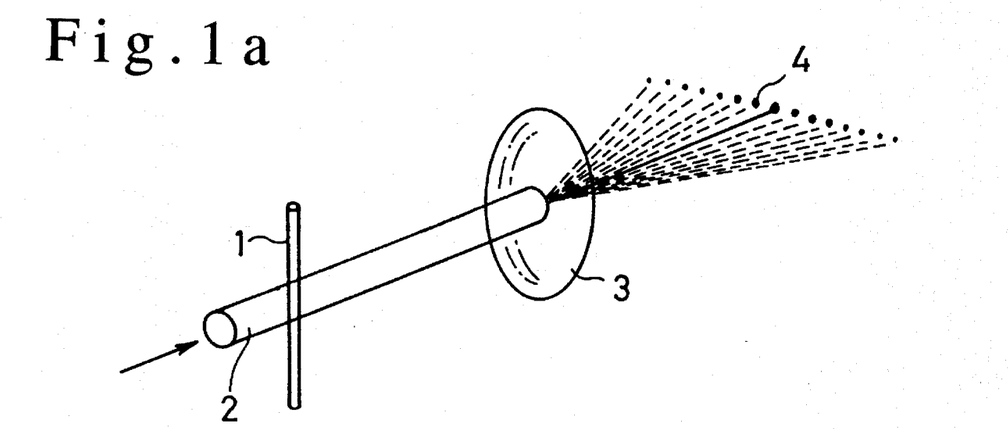
FIG. 1a is a perspective view illustrating that a diffraction pattern is formed when laser light is irradiated onto yarn.

The modes of embodiment of the present invention will now be described in detail based on the drawings.
Optical principle Firstly, in describing the basic optical principle of the present invention, as shown in FIG. 1a, when laser light 2 is irradiated such that it intersects yarn 1, and the diffracted light which has passed through the yarn 1 is then passed through a convex lens 3, a diffraction pattern 4, aligned in the form of dots, will appear on a screen which is separated by a distance equal to the focal length of the convex lens.

Figure 1B:
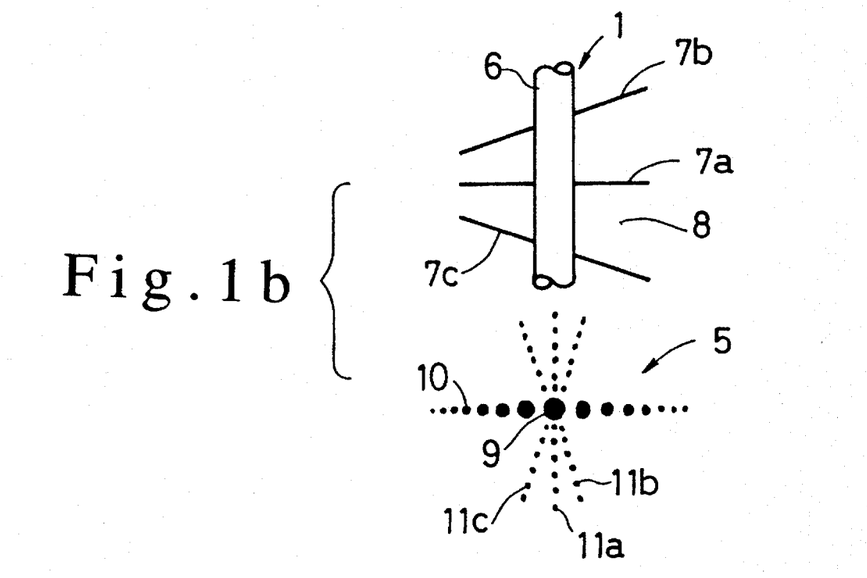
FIG. 1b is a diagram showing the correlation between hairy yarn and the Fourier transformation pattern formed when diffracted light which has passed through said yarn is subjected to a Fourier transformation.

Then, by making use of this principle, by passing the laser light through a beam enlargement lens and irradiating the enlarged parallel rays of light onto the yarn, and then focusing the diffracted light which has passed through the yarn by passing it through a convex lens, a Fourier transformation pattern 5, as shown in FIG. 1b, appears on a spectrum plane which is located in the focal plane of said convex lens, by means of a Fourier transformation. With yarn 1 which has a core part 6 and a hairy part 7, the Fourier transformation pattern 5 contains a pattern center part 9 which is formed due to the background part 8 between the hairs, a core part pattern 10 in the form of dots, extending from said pattern center part 9 in the left and right directions, formed due to the core part 6, and a surface projection pattern 11 in the form of dots, extending from said pattern center part 9 in the radial direction, formed due to the hairy part 7. In the Fourier transformation pattern 5, a hair 7a, from among the hairs, which projects from the core part 6 at right angles appears as a pattern 11a extending from the pattern center part 9 in the vertical direction, in other words extending such that it intersects the core part pattern 10 at right angles. Further, a hair 7b which is inclined in the anticlockwise direction with respect to said perpendicular hair 7a appears as a pattern 11b in a position which is displaced in the anticlockwise direction with respect to said perpendicular pattern 11a. On the other hand, a hair 7c which is inclined in the clockwise direction with respect to said perpendicular hair 7a appears as a pattern 11c in a position displaced in the clockwise direction with respect to said perpendicular pattern 11a.

If the core part 6 of the yarn 1 is thin then the shape of each point which appears in the core part pattern 10 is altered such that it is widened in the direction of said pattern, and the series of dots is altered to become coarse. Conversely, if the core part 6 is thick then the shape of each point which appears in the core part pattern 10 will be altered such that it is contracted in the direction of said pattern, and the series of points is altered such that they become dense.

Similarly, with regard to the hairy parts 7, if the hairs 7a, 7b and 7c are thin then the shape of each point which appears in the respective patterns 11a, 11b and 11c is altered such that they are widened in the direction of said pattern, and the series of dots is altered such that it becomes coarse. Conversely, if the hairs 7a, 7b and 7c are thick then the shape of each point which appears in said patterns 11a, 11b and 11c will alter such that they are contracted in the direction of said pattern, and the series of points will become dense.

It is thus possible to detect thick and/or thin irregularities of the core part 6 of the yarn 1 from the Fourier transformation pattern 5, by detecting and analyzing the core part pattern 10. Further, it is possible to detect the state of the hairs 7a, 7b and 7c separately by detecting and analyzing the surface projection patterns 11a, 11b and 11c.

Figure 1C:
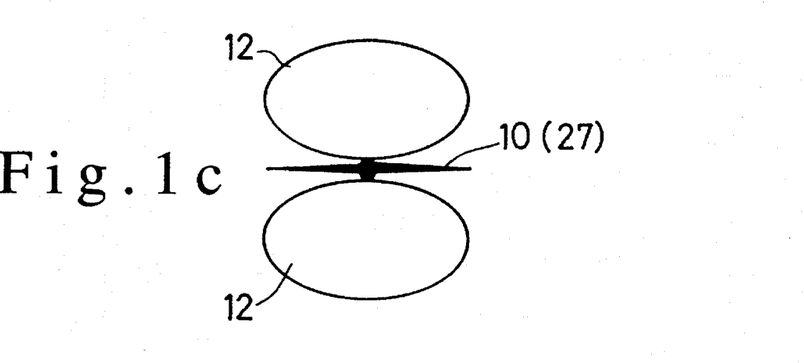
FIG. 1c is an explanatory diagram showing an example of the analysis of the Fourier transformation pattern.

Alternatively, it is understood that instead of detecting each hair 7a, 7b and 7c which projects from the surface of the core part 6 individually, it is sufficient, in order to measure the overall state of the hairy part 7 which contains these fibres, to detect and analyze the surface pattern region 12 which is occupied by the surface projection patterns 11a, 11b and 11c in the Fourier transformation pattern 5, as shown schematically in FIG. 1c.

Thus, by analyzing said Fourier transformation pattern 5 it is possible to measure three states, namely the state of the core part 6 of the yarn 1, the states of each hair 7a, 7b and 7c, and the overall state of the hairy part 7.

First mode of embodiment

Figure 2:
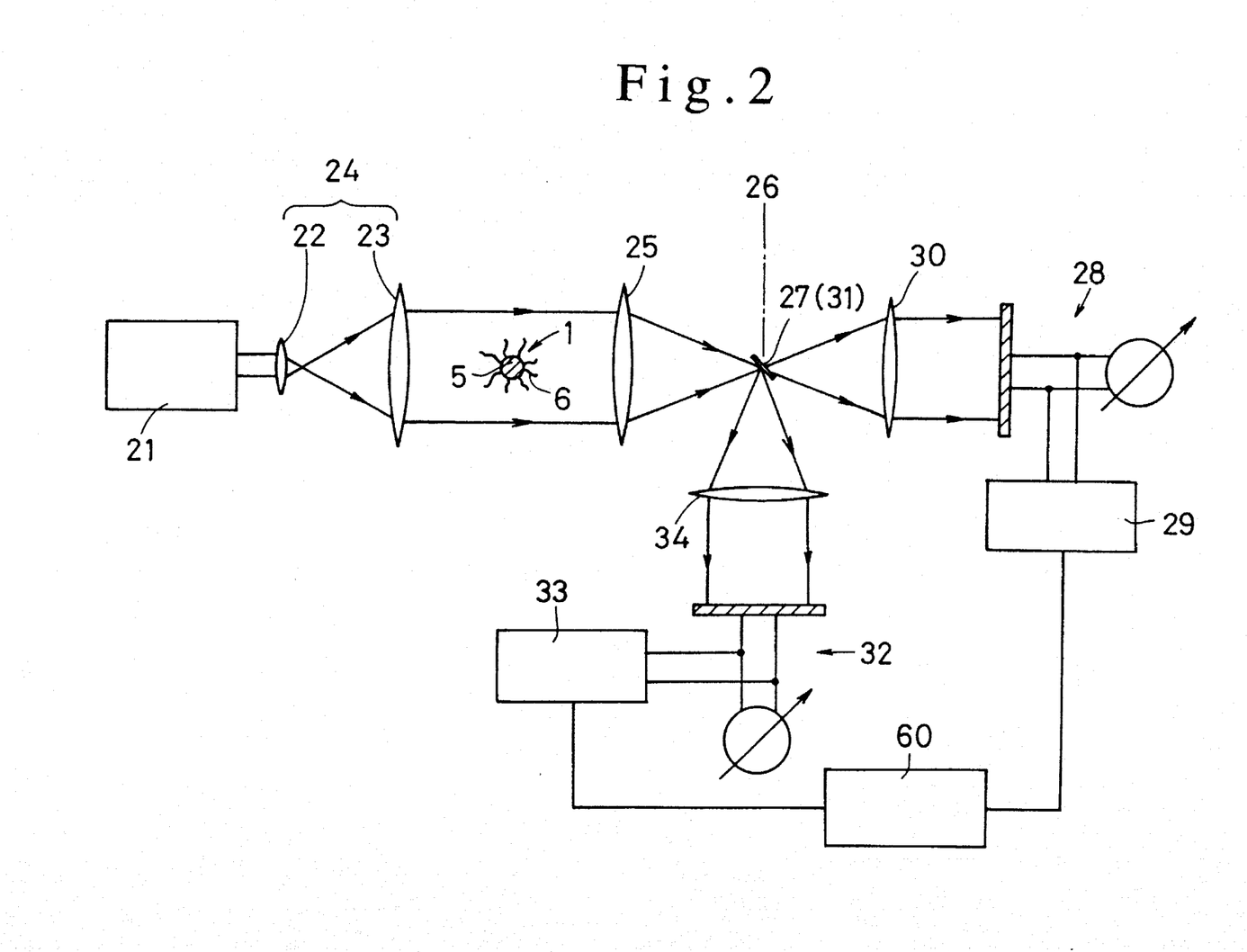
FIG. 2 is a schematic diagram showing a first embodiment of a yarn measuring device according to the present invention.

FIG. 2 shows a first mode of embodiment of the device according to the present invention, and there is provided a laser output means 21 which radiates laser light such that it intersects traveling yarn 1. The laser output means 21 is a known output means such as a gas laser, a solid laser or a semiconductor laser, and a commercially available device can be used.

Laser light output from the laser output means 21 is subjected to light-ray enlargement and parallelization by means of a beam enlargement lens means 24 which includes a pair of lenses 22 and 23, and the light is then irradiated towards the yarn 1. The laser light thus passes the entire core part 6 and hairy part 7 of the yarn 1, thereby forming diffracted light.

Diffracted light which has passed the yarn 1 is led to a Fourier transformation convex lens 25 where it is subjected to a Fourier transformation, and is then focused on a spectrum plane 26 which is positioned at the focal point of said lens 25. A Fourier transformation pattern 5 such as that shown in FIG. 1b then forms on the spectrum plane 26.

A removal means 27 which removes the core part pattern 10 from the Fourier transformation pattern 5 is provided on said spectrum plane 26. The removal means 27 may be constructed from a long thin member which acts as a shield such that the core part pattern 10 shown in FIG. 1b does not pass the spectrum plane 26, and it should have a shape which coincides with the shape which covers the whole of the core part pattern 10 as shown in FIG. 1c. Thus only the surface projection pattern 11 which remains after the core part pattern 10 has been removed from the Fourier transformation pattern 5 passes through the spectrum plane 26.

The surface projection pattern 11 which has passed through said spectrum plane 26 is received and analyzed by means of a first light detecting means 28.

Two methods can be formulated in order to perform analysis using the first light detecting means 28. According to a first method, all of the light contained in a surface pattern region 12 which combines the surface projection patterns 11a, 11b and 11c, which indicate the hairs 7a, 7b and 7c of the yarn 1 shown in FIGS. 1b and 1c, is received, the total quantity of light and/or the light intensity are measured by means of the first light detecting means 28, and by this means the overall state of the hairy part 7 of the yarn 1 is evaluated. To this end, the construction should be such that diffracted light in the surface pattern region 11 which has passed through the spectrum plane 26 is led directly to the first light detecting means 28, for example the first light detecting means 28 should consist of an optical sensor such as a photodiode, and a measuring means 29 which performs an A/D conversion on the output from said optical sensor and evaluates the output should be provided.

According to a second method, each of the hairs 7a, 7b and 7c indicated by the surface projection patterns 11a, 11b and 11c is measured individually by a first light detecting means 28. To this end, as shown in FIG. 2, the surface projection patterns 11a, 11b and 11c which have passed through the spectrum plane 26 should be led to a reverse Fourier transformation convex lens 30 which performs a reverse Fourier transformation, and measurement and evaluation should be performed, using the images of the hairs 7a, 7b and 7c which have been formed by said reverse transformation as the image, by means of the first light detecting means 28. For example, the first light detecting means 28 may consist of an image processing means such as a CCD scanning line camera, a CCD matrix camera or a television camera, and the image may be recorded without further modification using an image recording means and evaluated digitally, and it is thus possible to evaluate the hairs 7a, 7b and 7c in detail.

The core part pattern 10 which has been removed from the abovementioned Fourier transformation pattern 5 by the removal means 27 is led by a guide means 31 in a direction refracted away from the spectrum plane 26. In the mode of embodiment shown by way of example in FIG. 2, the core part pattern 10 which has been removed is led in a perpendicular refracted angle, but this angle need not be a right angle. The guide means 31 may be constructed such that the core part pattern 10 is reflected by means of a mirror formed on the surface of said removal means 27, and it may also be constructed such that the core part pattern 10 which is incident on the removal means 27 is refracted by means of a prism.

The core part pattern 10 which has been led by means of said guide means 31 is received by a second light detecting means 32 and is analyzed.

In order to perform analysis using the second light detecting means 32, two methods can be formulated, in the same or similar way as in the first light detecting means 28 described above. According to a first method, the core part pattern 10 is received, the quantity of light and/or light intensity of the pattern 10 are measured by means of the second light detecting means 32 so that thick irregularities and/or thin irregularities, for example, of the core part 6 of the yarn 1 are evaluated. To this end, the construction may be such that the refracted light of the core part pattern 10 which has been led by means of the guide means 31 is led directly to the second light detecting means 32, and for example the second light detecting means 32 may consist of an optical sensor such as a photodiode, and a measuring means 33 which performs an A/D conversion on the output from said optical sensor and evaluates the output may be provided.

According to a second method, the core part 6 indicated by the core part pattern 10 is measured as an image by means of the second light detecting means 32. To this end, as shown in FIG. 2, the core part pattern 10 which has been led from the guide means 31 should be led to a reverse Fourier transformation convex lens 34 which performs a reverse Fourier transformation, and measurement and evaluation should be performed by means of the second light detecting means 32, with the image of the core part 6, which has been formed by means of said reverse transformation, as the image. For example, the second light detecting means 32 may consist of an image processing means such as a CCD scanning line camera, a CCD matrix camera or a television camera, and the image may be recorded without further modification by leans of an image recording means, and evaluated digitally, and it is thus possible to evaluate thick irregularities and/or thin irregularities, for example, of the core part 6.

In a first mode of embodiment of the present invention based on FIG. 2, the description outlined above indicated a construction in which the surface projection patterns 11a, 11b and 11c from the Fourier transformation pattern 5 which had passed through the spectrum plane 26 without being removed by the removal means 27 were detected by means of the first light detecting means 28, while the core part pattern 10 which had been removed by the removal means 27 and led by the guide means 31 was detected by means of the second light detecting means 32, but a construction may also be used whereby the removal of the pattern is reversed. In other words it is also possible to have a construction in which the surface projection patterns 11a, 11b and 11c from the Fourier transformation pattern 5 are removed by the removal means 27, and the core part pattern 10 which passes through the spectrum plane 26 without being removed is detected by means of the first light detecting means 28, while the surface projection patterns 11a, 11b and 11c which have been removed by means of the removal means 27 are led to the second light detecting means 32 by the guide means 31. In this case the removal means 27 may comprise a shield plate provided with a slit which only allows the core part pattern 10 to be transmitted, and the guide means 31 may consist of a mirror which reflects the surface projection patterns 11a, 11b and 11c which have been received by the shield plate around said slit, in a direction refracted from the spectrum plane 26, or a prism which causes refraction.

According to the construction mentioned above, it is possible to measure simultaneously and in parallel the state of the core part 6 and the state of the hairy part 7 of a traveling yarn 1, and it is therefore possible to perform detailed measurement inspections of hairy yarn 1. In other words, it is possible to perform measurement inspections relating to the hairy part of the yarn and to perform measurement inspections relating to the core part, for example thick irregularities and/or thin irregularities of the yarn.

Furthermore, it is possible to make use of the data for the surface projection patterns 11a, 11b and 11c which have been detected by means of the first light detecting means 28, and the data for the core part pattern 10 which has been detected by the second light detecting means 32, such that one set of data is corrected by means of the other set of data. For example, if measurement inspections are to be performed only on the hairy part 7 of the yarn then it is possible to make use of the data relating to the core part 6 which has been measured simultaneously, in order to correct the data for the hairy part 7.

In theory, when measuring the hairy part 7 of the yarn, the first light detecting means 28 receives only the surface projection pattern 11 of the Fourier transformation pattern 5, from which the core part pattern 10 has been removed, and it is therefore possible to perform accurate evaluation of the hairy part 6 by analyzing this pattern. However, in an actual device, stray light resulting from dispersed and reflected light, for example, at the lens surface of the Fourier transformation convex lens 25 passes through the spectrum plane and enters the light path formed by means of a pipe-shaped housing or the like, and there is a danger that light other than the surface projection pattern 11 will be received by the first light detecting means 28, and therefore accurate evaluation of the hairy part 7 is difficult. It is thus preferable to eradicate the effects of said stray light by correcting the data based on the surface projection patterns 11a, 11b and 11c which have been detected by means of the first light detecting means 28, using the data based on the core part pattern 10 which has been detected by means of the second light detecting means 32, and in this way it is possible to evaluate the hairy part 7 accurately.

To elaborate, provided that no light enters the device from outside, the quantity of light based on the surface projection pattern 11 which has been received by the first light detecting means 28, and the quantity of light based on the core part pattern 10 which has been received by the second light detecting means 32 are proportional to the thicknesses of the core part 6 and the hairy part 7 of the yarn 1, based on the total quantity of light of the two. Thus the quantity of stray light received by the first light detecting means 28 in addition to the quantity of light based on the surface projection pattern 11 is proportional to the thickness of the core part 6 of the yarn 1. Thus, by correcting the data detected by the first light detecting means 28, by means of data relating to variations in the thickness of the core part 6 detected by means of the second light detecting means 32, it is possible to evaluate the hairy part 7 accurately, without the stray light having an effect.

Such data correction can be achieved by means of the following method, for example.

If the thickness of the yarn under observation is D and the amount of hair is H, then the output signal $S_1$ from the first light detecting means 28, which has observed the amount of hair, is expressed by the following formula (1).

$$S_1 = \alpha_1 = D + \beta_1 H \qquad \text{formula (1)}$$

Thus the output signal $S_1$ contains stray light due to the thickness D of the yarn ($\alpha_1$ is a stray light coefficient). It should be noted that $\beta_1$ is a conversion coefficient for the conversion of the quantity of light due to the amount of hair H into an electrical output.

Meanwhile, the output signal $S_2$ from the second light detecting means 32 which has observed the thickness of the yarn is expressed by the following formula (2).

$$S_2 = \alpha_2 D + \beta_2 H \qquad \text{formula (2)}$$

The output signal $S_2$ thus contains stray light due to the hairs H of the yarn ($\beta_2$ is a stray light coefficient). It should be noted that $\alpha_2$ is a conversion coefficient for the conversion of the amount of light due to the thickness D into an electrical output.

Furthermore, prior to observation of traveling yarn, the following data 1 and 2 are obtained as calibration data.
(Calibration data 1)

Calibration data 1 are obtained by measuring a rod-shaped specimen which has no hair. The thickness of the rod-shaped specimen is $D_0$ but since there is no hair, H=0. Thus the output data produced from the first light detecting means 28, and the output data $S_{20}$ produced from the second light detecting means 32 are respectively expressed by the following formulae (3) and (4).

$$S_{10} = \alpha_1 D_0, \text{ therefore } \alpha_1 = S_{10}/D_0 \qquad \text{formula (3)}$$

$$S_{20} = \alpha_2 D_0, \text{ therefore } \alpha_2 = S_{20}/D_0 \qquad \text{formula (4)}$$

(Calibration data 2)

Calibration data 2 are obtained by measuring a specimen which has a constant amount of hair and which has a core part which does not vary and which is uniform. The specimen has a constant thickness $D_0$ and a constant amount of hair $H_0$. The output data $S_{11}$ obtained from the first light detecting means 28, and the output data $S_{21}$ obtained from the second light detecting means 32 are expressed respectively by means of the following formulae (5) and (6).

$$S_{11} = \alpha_1 D_0 + \beta_1 H_0 = S_{10} + \beta_1 H_0$$

therefore $$\beta_1 = (S_{11} - S_{10})/H_0 \qquad \text{formula (5)}$$

$$S_{21} = \alpha_2 D_0 + \beta_2 H_0 = S_{20} = \beta_2 H_0$$

therefore $$\beta_2 = (S_{21} - S_{20})/H_0 \qquad \text{formula (6)}$$

Thus by substituting the calibration data 1 (formulae (3) and (4)) and the calibration data 2 (formulae (5) and (6)), which were obtained as outlined above, into the observed values for the traveling yarn which have been detected by means of the first light detecting means 28 and the second light detecting means 32, in other words into the abovementioned formulae (1) and (2), it is possible to express the output $S_1$ from the first light detecting means 28 by means of the following equation (7-1), and the output $S_2$ from the second light detecting means 32 by means of the following equation (7-2). The values $D/D_0$ and $H/H_0$ thus become clear, as shown by the following equation (7-3) and equation (7-4), and it is thus possible to eradicate the stray light due to the thickness of the yarn, which is included in the output from the first light detecting means 28, and the stray light due to the hairs, which is included in the output from the second light detecting means 32.

$$S_1 = \frac{S_{10}}{D_0} \cdot D + \frac{S_{11} - S_{10}}{H_0} \cdot H = S_{10} \cdot \frac{D}{D_0} + (S_{11} - S_{10}) \cdot \frac{H}{H_0} \qquad \text{Equation (7-1)}$$

$$S_2 = \frac{S_{20}}{D_0} \cdot D + \frac{S_{21} - S_{20}}{H_0} \cdot H = S_{20} \cdot \frac{D}{D_0} + (S_{21} - S_{20}) \cdot \frac{H}{H_0} \qquad \text{Equation (7-2)}$$

$$\frac{D}{D_0} = \frac{S_{21} - S_{20}}{S_{10}S_{21} - S_{20}S_{11}} \cdot S_1 + \frac{S_{10} - S_{11}}{S_{10}S_{21} - S_{20}S_{11}} \cdot S_2 \qquad \text{Equation (7-3)}$$

$$\frac{H}{H_0} = \frac{-S_{20}}{S_{10}S_{21} - S_{20}S_{11}} \cdot S_1 + \frac{S_{10}}{S_{10}S_{21} - S_{20}S11} \cdot S_2 \qquad \text{Equation (7-4)}$$

Correction of the data above mentioned can be achieved easily by providing a correction means 60 such as a calculating means. Thus in the mode of embodiment of the present invention, as shown in FIG. 2, a correction means 60 which corrects, based on the pattern data detected by means of the first light detecting means 29 and the pattern data detected by means of the second light detecting means 32, one set of data using the other set of data is provided.

The correction means 60 may correct the data for the surface projection patterns 11a, 11b and 11c by means of the core part pattern 10 data in order to evaluate the hairy parts 7 correctly, or conversely it may correct the data for the core part pattern 10 by means of the data for the surface projection patterns 11a, 11b and 11c in order to evaluate the core part 6 accurately.

As outlined above, in a device in which the first light detecting means 28 and the second light detecting means 32 consist of optical sensors such as photodiodes, and the light intensities of the patterns received thereby are subjected to A/D conversion and analyzed, it is possible to construct said correction means 60 using a differential amplifier.

On the other hand, the device in which the first light detecting means 28 and the second light detecting means 32 are constructed by means of an image processing means such as a CCD camera, it is possible to provide a circuit which, based on said correction means 60, corrects images whose contours have been blurred by stray light, such that the contours are sharp.

Embodiment

Figure 3:
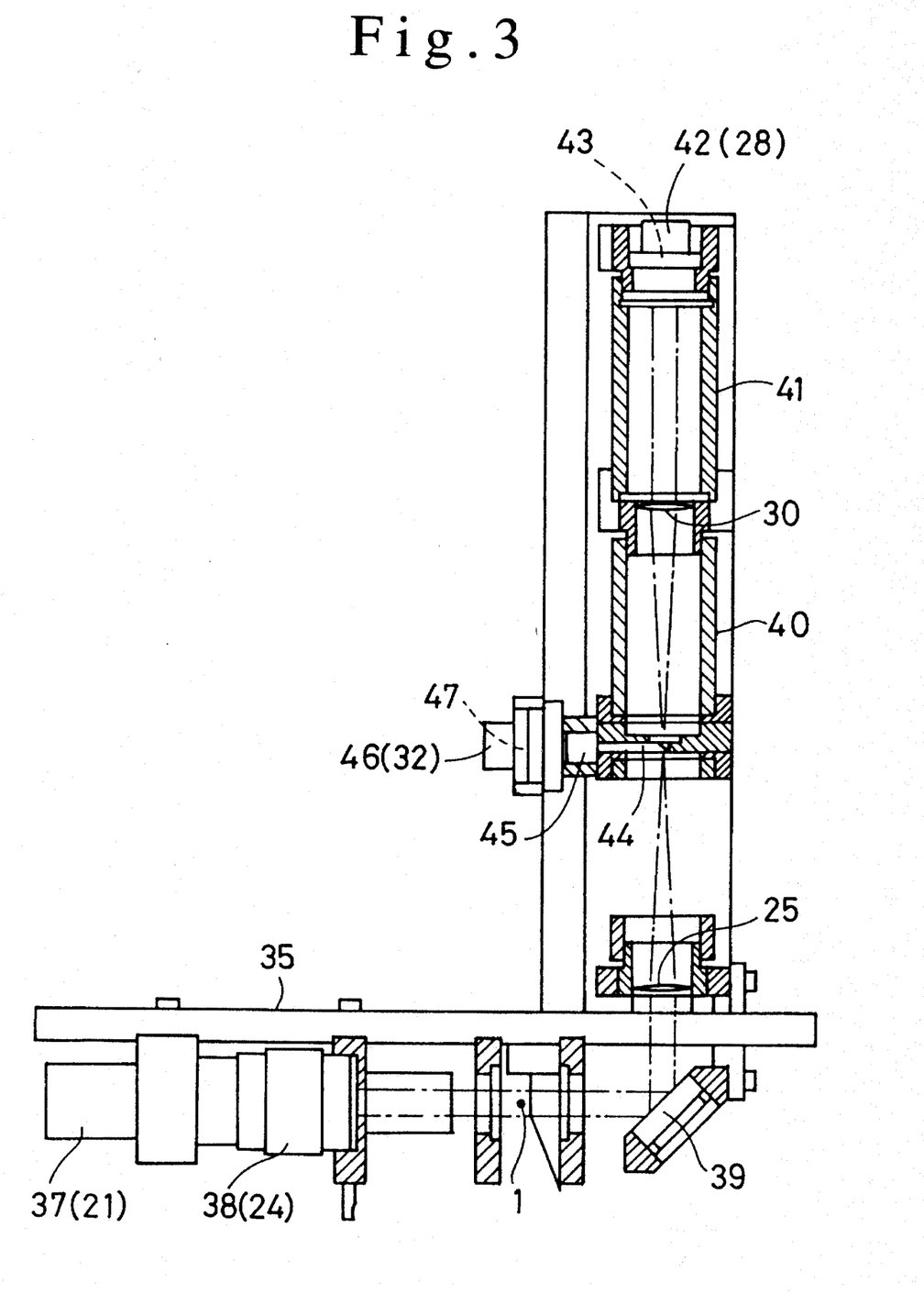
FIG. 3 is a cross sectional view showing a first embodiment of a device which has been realized based on the first mode of embodiment of the present invention.

FIG. 3 shows an embodiment based on the abovementioned first mode of embodiment. A laser output means 21 consisting of a laser diode 37 is provided on one frame 35 of a pair of frames 35 and 36 which are arranged perpendicular to each other, and a beam expander 38 with a built-in lens means 24 is attached to the tip thereof. There is provided a yarn guide (not shown) which guides yarn 1 such that it intersects a laser light beam which has been expanded, made parallel and output by means of said beam expander 38, and diffracted light which has passed the yarn 1 is reflected in a perpendicular direction by means of a mirror 39 and is guided parallel to the other frame 36.

The diffracted light which has been guided by said mirror 39 is subjected to a Fourier transformation by means of a Fourier transformation convex lens 25. A wire-shaped removal means 27 (not shown) is arranged positioned in the focal plane (spectrum plane) of said convex lens 25, and this acts as a shield such that the core part pattern 10 of the Fourier transformation pattern 4 does not pass through the spectrum plane. The remaining pattern from which the core part pattern 10 has been removed, in other words the surface projection patterns 11a, 11b and 11c, passes through the spectrum plane, then passes through a light path consisting of a first pipe member 40 and a second pipe member 41, and reaches a light reception surface 43 of a first light detecting means 28 which consists of a photodiode 42. A reverse Fourier transformation convex lens 30 is arranged between said first pipe member 40 and second pipe member 41, and thus the surface projection patterns 11a, 11b and 11c which pass through the spectrum plane reach the photodiode 42 in the form of an image of the hairy part 7. It should be noted that the quantity of light detected by the photodiode 42 is subjected to A/D conversion and is evaluated by means of a computer.

The core part pattern 10 which has been removed by the removal means 27 at the spectrum plane is guided in the direction of the light path by means of a beam sampler 45 which is provided with a prism 44, and it reaches a light reception surface 47 of a second light detecting means 32 which consists of a photodiode 46, and the quantity of light which is detected at this point is subjected to A/D conversion and is evaluated by means of a computer.

It should be noted that, although omitted from the diagram, the data based on the quantity of light detected by means of the first light detecting means 28, and the data based on the quantity of light detected by the second light detecting means 32 pass through a correction means comprising a differential amplifier, for example, as outlined above, and one set of data is corrected by means of the other set of data.

Second mode of embodiment

Figure 4:
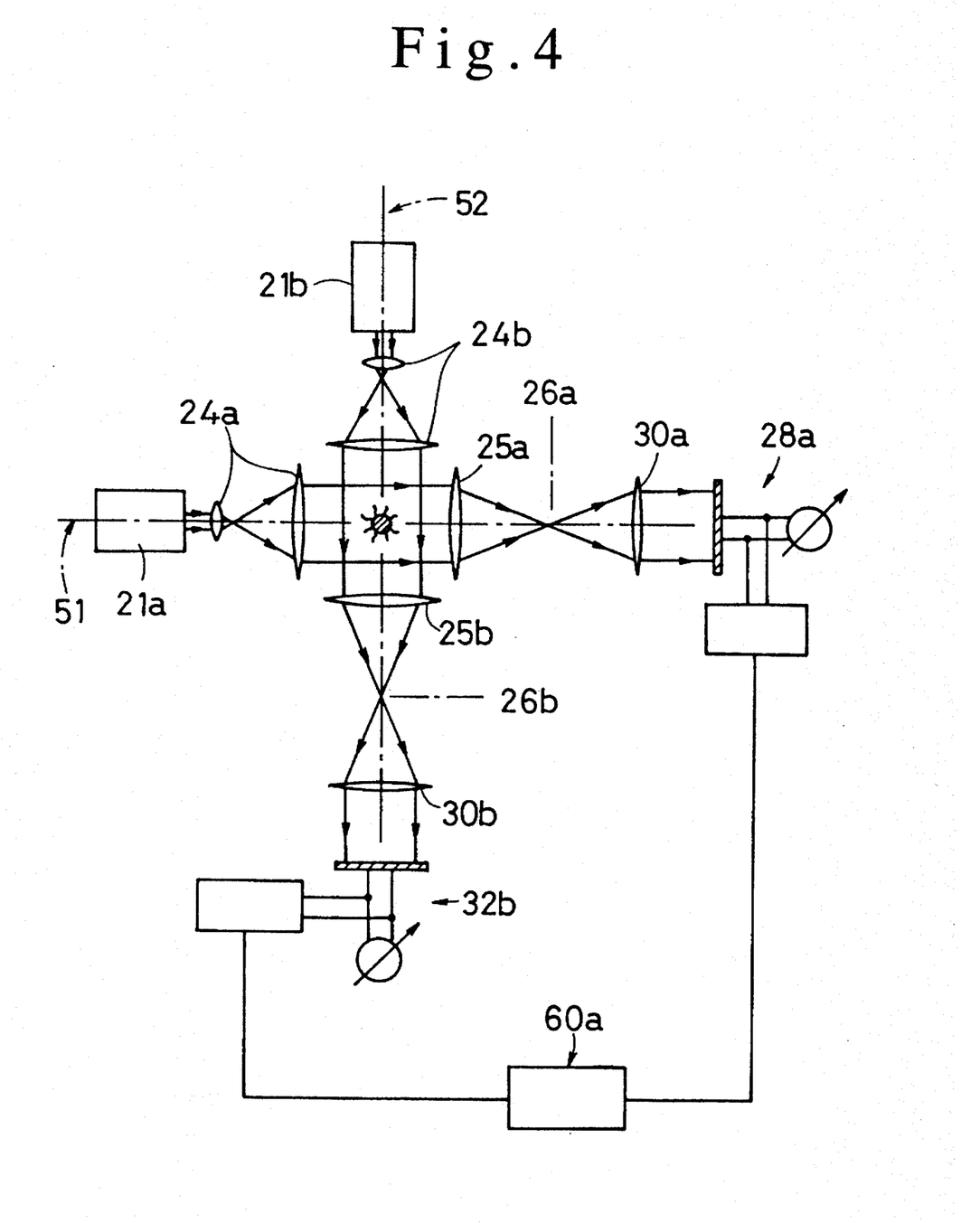
FIG. 4 is a schematic diagram showing a second mode of embodiment of a yarn measuring device according to the present invention.

FIG. 4 shows a second mode of embodiment of the device according to the present invention, and it consists of a combination of a yarn surface state measuring device 51 and a yarn core state measuring device 52.

The yarn surface state measuring device 51 is provided with a first laser output means 21a which irradiates laser light such that it intersects traveling yarn 1, and a first beam enlargement lens means 24a which includes a pair of lenses which expand and make parallel the laser light output from said laser output means 21a, and it irradiates the enlarged beam such that it intersects the yarn 1. Diffracted light which has passed through the yarn 1 is subjected to a Fourier transformation by means of a first Fourier transformation convex lens 25a, and a first Fourier transformation pattern is formed on a spectrum plane 26a which is positioned at the focal point of said convex lens 25a. This pattern is the same as the pattern 5 shown in FIG. 1b, and contains a core part pattern 10 and a surface projection part 11 of the yarn, as outlined above.

The core part pattern 10 from said Fourier transformation pattern 5 is then removed by means of a first removal means (not shown) which is located on the spectrum plane 26a. Thus only the remaining surface projection pattern 11 passes through the spectrum plane 26a, and a first light detecting means 28a which receives the surface projection pattern 11 is provided.

If necessary, a first reverse Fourier transformation convex lens 30a which performs a reverse Fourier transformation on the surface projection pattern 11 which is passed through the first removal means may be provided, and it is possible to send the surface projection pattern 11 to the first light detecting means 28a in the form of an image of the hairs 7.

The first light detecting means 28a has the same construction as the first light detecting means 28 in the first mode of embodiment described with reference to FIG. 2.

The yarn core state measuring device 52 is arranged such that it intersects said device 51 at the yarn 1 part, and is provided with a second laser output means 21b which irradiates laser light such that it intersects the yarn 1 from a different angle to that of said first laser output means 21a, and a second beam enlargement lens means 24b which includes a pair of lenses which expand and make parallel the laser light output from the second laser output means 21b. Diffracted light which has passed through the yarn 1 is subjected to a Fourier transformation by means of a second Fourier transformation convex lens 25b, and a second Fourier transformation pattern is formed on a spectrum plane 26b which is positioned at the focal point of said convex lens 25b. This pattern includes a core part pattern 10 and a surface projection pattern 11 of the yarn, as shown in FIG. 1b.

The surface projection pattern 11 from said Fourier transformation pattern 5 is removed by means of a second removal means (not shown) which is provided on said spectrum plane 26b. Thus only the remaining core part pattern 10 passes through the spectrum plane 26b, and there is provided a second light detecting means 32b which receives the core part pattern 10.

If necessary, a second reverse Fourier transformation convex lens 30b which performs a reverse Fourier transformation on the core part pattern 10 which has passed through the second removal means may be provided, and it is thus possible to send the core part pattern 10 to the second light detecting means 32b in the form of an image of the core part 6 of the yarn.

The second light detecting means 32b has the same construction as the second light detecting means 32 in the first mode of embodiment which was described with reference to FIG. 2.

There is furthermore provided a correction means 60a which, based on the data for the surface projection pattern 11 which was detected by means of the first light detecting means 28a and the data for the core part pattern 10 which was detected by means of the second light detecting means 32b, corrects one set of data by means of the other set of data. The correction means 60a has the same construction as the correction means 60 in the first mode of embodiment which was described based on FIG. 2.

Mode of use of the device

Either of the first mode of embodiment and the second mode of embodiment outlined above can perform simultaneous parallel measurement of the state of the core part 6 and the state of the hairy part 7 of traveling yarn 1, and it is therefore possible to perform detailed measurement inspections of hairy yarn 1. In particular, it is possible to perform measurement inspections relating to the hairy part of the yarn, and to perform measurement inspections relating to the core part, for example thick irregularities and/or thin irregularities of the yarn.

Furthermore, if, as outlined above, correcting means 60 and 60a are provided, then it is possible, based on the pattern data detected by means of the first light detecting means 28 and 28a, and the pattern data detected by means of the second light detecting means 32 and 32b, to correct one set of data by means of the other set of data, and it is thus possible to eradicate the effects of stray light which occur within the device, and thus accurate evaluation of the core part 6 and/or the hairy part 7 is achieved.

The device of the present invention is principally used for measuring yarn which has hair, but its use is not limited to hairs, and it may also be used widely in order to measure linear objects on the surface of which long thin projections are formed.

Advantages of the Invention

According to the present invention it is possible to measure accurately the state of the core part 6 and the hairy part 7 of yarn individually, by employing laser light.

Furthermore, according to the present invention it is possible, based on data for the core part 6 and data for the hairy part 7, which data have been detected independently, to correct one set of data by means of the other set of data, when measuring the state of the core part 6 and/or the hairy part 7 of the yarn, and it is therefore possible to eliminate the effects of stray light and the like which occur due to lens surfaces, and to perform accurate evaluation of the core part 6 and/or the hairy part 7.

What is claimed is:

1. A yarn measuring device comprising a laser light output means (21) which emits laser light in such a manner that it intersects traveling yarn (1); a Fourier transformation convex lens (25) which forms a Fourier transformation pattern, including a core part pattern and a surface projection pattern of the yarn, on a spectrum plane (26) by performing a Fourier transformation of diffracted light which has passed through the yarn; a removal means (27) which is located on said spectrum plane and removes one of the core part pattern and the surface projection pattern in the Fourier transformation pattern; a first light detecting means (28) which receives the other pattern which has passed through the spectrum plane and has not been removed by said removal means; a guide means (31) which leads the pattern which has been removed by said removal means in a direction which is refracted from the spectrum plane; and a second light detecting means (32) which receives the pattern which has been led by said guide means.

2. A yarn measuring device according to claim 1, wherein there is provided a correction means (60) which, based on the pattern data detected by the first light detecting means (28) and the pattern data detected by the second light detecting means (32), corrects one set of data by means of the other set of data.

3. A yarn measuring device according to claim 1 or 2, wherein there is provided a reverse Fourier transformation convex lens (30) which performs a reverse Fourier transformation on the other pattern which has passed through the spectrum plane and has not been removed by the removal means, whereby a partial image of the yarn, formed by means of said reverse transformation, is detected by the first light detecting means (28).

4. A yarn measuring device according to claim 1 or 2, wherein there is provided a reverse Fourier transformation convex lens (34) which performs a reverse Fourier transformation on the pattern which has been led by the guide means (31), whereby a partial image of the yarn, formed by means of said reverse transformation, is detected by means of the second light detecting means (32).

5. A yarn measuring device comprising a yarn surface state measuring device (51) having a first laser output means (21a) which emits laser light in such a manner that it intersects traveling yarn (1); a first Fourier transformation convex lens (25a) which forms a first Fourier transformation pattern, including a core part pattern and a surface projection pattern of the yarn, on a first spectrum plane (26a) by performing a Fourier transformation on diffracted light which has passed through the yarn; a first removal means which is located on said first spectrum plane and removes the core part pattern from the Fourier transformation pattern; and a first light detecting means (28a) which receives the surface projection pattern which has passed through said first removal means;

a core state measuring device (52) having a second laser output means (21b) which emits laser light in such a manner that it intersects said yarn (1) from an angle which is different from that of said first laser output means; a second Fourier transformation convex lens (25b) which forms a second Fourier transformation pattern, including a core part pattern and a surface projection pattern of the yarn, on a second spectrum plane (26b) by performing a Fourier transformation of diffracted light which has passed through the yarn; a second removal means which is located on said second spectrum plane and removes the surface projection pattern from the Fourier transformation pattern; and a second light detecting means (32b) which receives the core part pattern which has passed through said second removal means; and a correcting means (60a) which, based on surface projection pattern data detected by the first light detecting means (28a) and core part pattern data detected by the second light detecting means (32b), corrects one set of data by means of the other set of data.

6. A yarn measuring device according to claim 5, wherein there is provided a first reverse Fourier transformation convex lens (30a) which performs a reverse Fourier transformation on the surface projection pattern which has passed through the first removal means, whereby a yarn surface projection image, formed by means of the abovementioned reverse transformation, is detected by the first light detecting means.

7. A yarn measuring device according to claim 5 or 6, wherein there is provided a second reverse Fourier transformation lens (30b) which performs a reverse Fourier transformation on the core part pattern which has passed through the second removal means, whereby a yarn core part image, formed by means of said reverse transformation, is detected by means of the second light detecting means.

* * * * *

UNITED STATES PATENT AND TRADEMARK OFFICE
CERTIFICATE OF CORRECTION

PATENT NO. : 5,615,014
DATED : March 25, 1997
INVENTOR(S) : Kazuhiko OKUDA

It is certified that error appears in the above-identified patent and that said Letters Patent is hereby corrected as shown below:

Column 8, line 36 should be changed to read "$S_1 = \alpha_1 D + \beta_1 H$"

Signed and Sealed this

Twenty-ninth Day of December, 1998

Attest:

BRUCE LEHMAN

Attesting Officer

Commissioner of Patents and Trademarks